(12) United States Patent
Miller et al.

(10) Patent No.: US 7,744,850 B2
(45) Date of Patent: Jun. 29, 2010

(54) UZM-22 ALUMINOSILICATE ZEOLITE, METHOD OF PREPARATION AND PROCESSES USING UZM-22

(75) Inventors: Mark A. Miller, Des Plaines, IL (US); Jaime G. Moscoso, Des Plaines, IL (US); Gregory J. Lewis, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 881 days.

(21) Appl. No.: 11/462,056

(22) Filed: Aug. 3, 2006

(65) Prior Publication Data

US 2008/0031810 A1    Feb. 7, 2008

(51) Int. Cl.
*C01B 39/04* (2006.01)
(52) U.S. Cl. ...................... 423/707; 423/705
(58) Field of Classification Search ............. 423/705, 423/707
See application file for complete search history.

(56) References Cited

U.S. PATENT DOCUMENTS

| | | | |
|---|---|---|---|
| 3,950,496 A | 4/1976 | Ciric | 423/328 |
| 4,683,214 A * | 7/1987 | Angevine et al. | 502/66 |
| 5,350,570 A * | 9/1994 | Schmitt | 423/705 |
| 6,419,895 B1 | 7/2002 | Lewis et al. | 423/718 |
| 6,776,975 B2 | 8/2004 | Wilson et al. | 423/713 |
| 2005/0095195 A1 | 5/2005 | Lewis et al. | 423/705 |

OTHER PUBLICATIONS

A.W. Breton, "A Priori Prediction of Zeolites: Case Study of the Structure-Directing Effects in the Synthesis of MTT-Type Zeolites", J. Am. Chem. Soc., 2007, 129(24), 7627-7637.*
Science, 247, 1319-1322 (1990).
Zeolites, 14, 635-642 (1994).

* cited by examiner

*Primary Examiner*—David M Brunsman
(74) *Attorney, Agent, or Firm*—Frank S Molinaro

(57) ABSTRACT

A new family of crystalline aluminosilicate zeolites has been synthesized. These zeolites are represented by the empirical formula.

$$M_m^{n+}R_r^{+}Al_{(1-x)}E_xSi_yO_z$$

where M is an alkali, alkaline earth, or rare earth metal such as lithium and strontium, R is a singly charged organoammonium cation such as the choline cation and E is a framework element such as gallium. These zeolites are similar to ZSM-18 but are characterized by unique x-ray diffraction patterns and compositions and have catalytic properties for carrying out various hydrocarbon conversion processes.

17 Claims, No Drawings

UZM-22 ALUMINOSILICATE ZEOLITE, METHOD OF PREPARATION AND PROCESSES USING UZM-22

FIELD OF THE INVENTION

This invention relates to a new family of aluminosilicate zeolites designated UZM-22. They are represented by the empirical formula of:

$$M_m^{n+}R_r^+Al_{(1-x)}E_xSi_yO_z$$

where M is an exchangeable cation such as lithium or strontium, R is a singly charged organoammonium cation such as choline and E is a framework element such as gallium.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

One particular zeolite, designated ZSM-18 was first disclosed by Ciric in 1976 (See U.S. Pat. No. 3,950,496). This patent describes the synthesis of ZSM-18 from a triquat structure directing agent, 2,3,4,5,6,7,8,9-octahydro-2,2,5,5,8,8-hexamethyl-1H-benzo[1,2-c:3,4-c:5,6-c]tripyrrolium trihydroxide (triquat 1). The ZSM-18 was found to have pore openings greater than 7 Å based on the adsorption of cyclohexane and Si/Al from 5 to 15. $Na^+$ was also employed in the form of sodium aluminate and helped balance the framework charge from within the pores. It was also noted that if the Si/Al ratio of the reaction mixture was less than 10, the resulting ZSM-18 was unstable to calcination. It wasn't until 1990 that the structure of ZSM-18 was reported by Lawton et. al., revealing 1-dimensional 12-ring pores with the expected 7 Å aperture along with a perpendicular 7-ring pore system (See Science, 247, 1319-1322 (1990). The structure also contained the first 3-rings observed in an aluminosilicate. The authors attempted to examine the role of the triquat cation in the synthesis of ZSM-18 by fitting the structure of the triquat within the 12-ring pore, finding it could only occupy very specific positions. This was interpreted as a strong templating effect by the triquat and that such bulky, multiply charged templating cations may be required to make the observed zeolite with the 3-rings.

In 1994, a new synthesis for ZSM-18 was disclosed by Schmitt (See U.S. Pat. No. 5,350,570) which used a different triquat, $[(Me_3N^+(CH_2)_2)_3N]*3\ OH^-$, (triquat 2). Schmitt pointed out that little had been done with ZSM-18 since 1976 because the triquat 1 was very expensive and difficult to make and because thermal decomposition during calcination often destroyed the ZSM-18 sample. The new triquat 2 also possesses the bulky 3-fold, multiply charged structure reminiscent of triquat 1, which is seen as a requirement to make ZSM-18 via a templating effect. While the thermal decomposition of ZSM-18 with triquat 2 did successfully yield stable protonic forms of ZSM-18; it is now 12 years later and still little has been done with ZSM-18. This is because while triquat 2 is more economical than triquat 1, it is stated in the '570 patent that it is derived from a fine chemical and therefore remains too expensive for convenient use. A "rational synthesis" route to ZSM-18 was also disclosed in 1994 (Zeolites, 14, 635-642 (1994)). This rational approach acknowledges the same difficulties enumerated in the '570 patent with respect to economical synthesis and thermal degradation of triquat 1. This paper also cites "the almost perfect fit" of the triquat 1 template in the 12-ring pore concluding that if a templating effect exists, it is present in ZSM-18. This idea is then used to select template alternatives to triquat 1, with various types of modeling leading to triquat 2 mentioned above and $[(Me_3N^+(CH_2)_2)_3CH]*3OH^-$triquat 3, which is the same as triquat 2, except with the central N replaced with C—H. Triquat 3 managed to produce ZSM-18 only in the presence of seeds while triquat 2 produced a low quality ZSM-18 directly, but a highly crystalline ZSM-18 when seeds were employed in the synthesis. Zeolite ZSM-18 is still not used or studied because of the difficulty and expense of its preparation.

In contrast to the art described above, applicants have successfully prepared a new family of materials designated UZM-22. The topology of the materials is similar to that observed for ZSM-18. The materials are prepared via the use of a simple commercially available structure directing agents, such as choline hydroxide, $[HO(CH_2)_2NMe_3]^+OH^-$, in concert with small amounts of $Sr^{2+}$, $Li^+$, or $Sr^{2+}$ and $Li^+$ together, using the Charge Density Mismatch Approach to zeolite synthesis (See US Patent Application Publication No. 2005/0095195).

SUMMARY OF THE INVENTION

As stated, the present invention relates to a new aluminosilicate zeolite designated UZM-22. Accordingly, one embodiment of the invention is a microporous crystalline zeolite having a three-dimensional framework of at least $AlO_2$ and $SiO_2$ tetrahedral units and an empirical composition in the as synthesized and anhydrous basis expressed by an empirical formula of:

$$M_m^{n+}R_r^+Al_{1-x}E_xSi_yO_z$$

where M is at least one exchangeable cation selected from the group consisting of alkali, alkaline earth, and rare earth metals, "m" is the mole ratio of M to (Al+E) and varies from 0.05 to about 1.2, R is a singly charged organoammonium cation selected from the group consisting of choline, ethyltrimethylammonium (ETMA$^+$), diethyldimethylammonium (DEDMA$^+$), trimethylpropylammonium, trimethylbutylammonium, dimethyldiethanolammonium, tetraethylammonium (TEA$^+$), tetrapropylammonium (TPA$^+$) and mixtures thereof, "r" is the mole ratio of R to (Al+E) and has a value of about 0.25 to about 2.0, "n" is the weighted average valence of M and has a value of about 1 to about 3, E is an element selected from the group consisting of gallium, iron, boron and mixtures thereof, "x" is the mole fraction of E and has a value from 0 to about 1.0, "y" is the mole ratio of Si to (Al+E) and varies from greater than 2 to about 12 and "z" is the mole ratio of O to (Al+E) and has a value determined by the equation:

$$z=(m \cdot n+r+3+4 \cdot y)/2$$

and is characterized in that it has the x-ray diffraction pattern having at least the d-spacings and intensities set forth in Table A:

TABLE A

| 2θ | d (Å) | I/Io % |
|---|---|---|
| 7.53-7.89 | 11.73-11.20 | vs |
| 9.35-9.71 | 9.45-9.10 | w |
| 11.01-11.37 | 8.03-7.78 | m |
| 13.22-13.53 | 6.69-6.54 | w-m |
| 13.41-13.77 | 6.60-6.43 | w-m |
| 15.35-15.63 | 5.77-5.66 | w |
| 17.28-17.68 | 5.13-5.01 | w-m |
| 18.32-18.72 | 4.84-4.74 | w-m |
| 18.89-19.33 | 4.69-4.59 | m |
| 20.33-20.69 | 4.36-4.29 | w-m |
| 21.07-21.51 | 4.21-4.13 | s-vs |
| 21.34-21.74 | 4.16-4.08 | s-vs |
| 22.24-22.67 | 3.99-3.92 | w-m |
| 22.71-23.15 | 3.91-3.84 | w-m |
| 23.21-23.65 | 3.83-3.76 | m |
| 25.58-26.19 | 3.48-3.40 | w |
| 26.38-26.89 | 3.38-3.31 | m |
| 26.73-27.17 | 3.33-3.28 | w-m |
| 27.41-27.77 | 3.25-3.21 | w-m |
| 28.49-28.85 | 3.13-3.09 | m |
| 29.10-29.47 | 3.07-3.03 | m |
| 30.09-30.51 | 2.97-2.93 | w |
| 30.42-30.82 | 2.94-2.90 | w |
| 31.06-31.54 | 2.88-2.83 | w-m |
| 32.15-32.54 | 2.78-2.75 | w |
| 32.31-32.82 | 2.77-2.73 | w |
| 32.69-33.13 | 2.74-2.70 | w |
| 32.98-33.49 | 2.71-2.67 | w |
| 33.80-34.36 | 2.65-2.61 | w |
| 34.82-35.35 | 2.57-2.54 | w |
| 35.73-36.17 | 2.51-2.48 | w-m |
| 37.91-38.56 | 2.37-2.33 | w | is thermally stable up to a temperature of greater than 400° C.

Another embodiment of the invention is a process for preparing the crystalline microporous zeolite described above. The process comprises forming a reaction mixture containing reactive sources of M, R, Al, Si and optionally E and heating the reaction mixture at a temperature of about 60° C. to about 175° C. for a time sufficient to form the zeolite, the reaction mixture having a composition expressed in terms of mole ratios of the oxides of:

$$aM_{2/n}O:bR_{2/p}O:1-cAl_2O_3:cE_2O_3:dSiO_2:eH_2O$$

where "a" has a value of about 0.05 to about 1.25, "b" has a value of about 1.5 to about 40, "c" has a value of 0 to about 1.0, "d" has a value of about 4 to about 40, "e" has a value of about 25 to about 4000.

Yet another embodiment of the invention is a hydrocarbon conversion process using the above-described zeolite. The process comprises contacting the hydrocarbon with the zeolite at conversion conditions to give a converted hydrocarbon.

DETAILED DESCRIPTION OF THE INVENTION

Applicants have prepared an aluminosilicate zeolite whose topological structure is related to MEI as described in *Atlas of Zeolite Framework Types*, which is maintained by the International Zeolite Association Structure Commission at http://topaz.ethz.ch/IZA-SC/StdAtlas.htm, which has been designated UZM-22. As will be shown in detail, UZM-22 is different from ZSM-18 in a number of its characteristics. The instant microporous crystalline zeolite (UZM-22) has an empirical composition in the as-synthesized form and on an anhydrous basis expressed by the empirical formula:

$$M_m^{n+}R_r^+Al_{1-x}E_xSi_yO_z$$

where M is at least one exchangeable cation and is selected from the group consisting of alkali, alkaline earth, and rare earth metals. Specific examples of the M cations include but are not limited to lithium, sodium, potassium, rubidium, cesium, calcium, strontium, barium, lanthanum, ytterbium and mixtures thereof. R is a singly charged organoammonium cation, examples of which include but are not limited to the choline cation, $[(CH_3)_3N(CH_2)_2OH]^+$, $ETMA^+$, $DEDMA^+$, trimethylpropylammonium, trimethylbutylammonium, dimethyldiethanolammonium, $TEA^+$, $TPA^+$ and mixtures thereof and "r" is the mole ratio of R to (Al+E) and varies from about 0.25 to about 2.0. The value of "n" which is the weighted average valence of M varies from about 1 to about 3 while "m" is the mole ratio of M to (Al+E) and varies from 0 to about 1.2. The ratio of silicon to (Al+E) is represented by "y" which varies from about 2 to about 12. E is an element which is tetrahedrally coordinated, is present in the framework and is selected from the group consisting of gallium, iron and boron. The mole fraction of E is represented by "x" and has a value from 0 to about 1.0, while "z" is the mole ratio of O to (Al+E) and is given by the equation:

$$z=(m \cdot n+r+3+4 \cdot y)/2.$$

Where M is only one metal, then the weighted average valence is the valence of that one metal, i.e. +1 or +2. However, when more than one M metal is present, the total amount of:

$$M_m^{n+}=M_{(m1)}^{(n1)+}+M_{(m2)}^{(n2)+}+M_{m3}^{(n3)+}+\ldots$$

and the weighted average valence "n" is given by the equation:

$$n = \frac{m_1 \cdot n_1 + m_2 \cdot n_2 + m_3 \cdot n_3 + \cdots}{m_1 + m_2 + m_3 \cdots}$$

The microporous crystalline zeolite, UZM-22, is prepared by a hydrothermal crystallization of a reaction mixture prepared by combining reactive sources of M, R, aluminum, silicon and optionally E. The sources of aluminum include but are not limited to aluminum alkoxides, precipitated aluminas, aluminum metal, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica and alkali silicates. Sources of the E elements include but are not limited to alkali borates, boric acid, precipitated gallium oxyhydroxide, gallium sulfate, ferric sulfate, and ferric chloride. Sources of the M metals include the halide salts, nitrate salts, acetate salts, and hydroxides of the respective alkali or alkaline earth metals. R is an organoammonium cation selected from the group consisting of choline, ETMA, DEDMA, TEA, TPA, trimethylpropylammonium, trimethylbutylammonium, dimethyldiethanolammonium and mixtures thereof, and the sources include the hydroxide, chloride, bromide, iodide and fluoride compounds. Specific examples include without limitation choline hydroxide and choline chloride, ethyltrimethylammonium hydroxide, diethyldimethylammonium hydroxide, tetraethylammonium hydroxide, tetrapropylammonium hydroxide, tetrapropylammonium chloride.

The reaction mixture containing reactive sources of the desired components can be described in terms of molar ratios of the oxides by the formula:

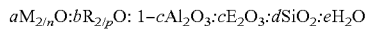

$aM_{2/n}O:bR_{2/p}O: 1-cAl_2O_3:cE_2O_3:dSiO_2:eH_2O$ where "a" varies from about 0.05 to about 1.25, "b" varies from about 1.5 to about 40, "c" varies from 0 to 1.0, "d" varies from about 4 to about 40, and "e" varies from about 25 to about 4000. If alkoxides are used, it is preferred to include a distillation or evaporative step to remove the alcohol hydrolysis products. The reaction mixture is now reacted at a temperature of about 60° C. to about 175° C. and preferably from about 80° C. to about 125° C. for a period of about 1 day to about 3 weeks and preferably for a time of about 4 days to about 14 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C. It should be pointed out that UZM-22 seeds can optionally be added to the reaction mixture in order to accelerate the formation of the zeolite.

A preferred synthetic approach to make UZM-22 utilizes the charge density mismatch concept, which is disclosed in US Patent Application Publication No. US 2005/0095195 and Studies in Surface Science and Catalysis, (2004), Vol. 154A, 364-372. The method disclosed in US 2005/0095195 employs quaternary ammonium hydroxides to solubilize aluminosilicate species, while crystallization inducing agents such as alkali and alkaline earth metals and more highly charged organoammonium cations are often introduced in a separate step. Once some UZM-22 seeds have been generated using this approach, the seeds can be used in a single step synthesis of UZM-22, using, for example, a combination of choline hydroxide and alkali and alkaline earth cations. The use of commercially available choline to prepare UZM-22 offers a great economic advantage over the structure directing agents previously employed (triquat 1 and triquat 2) to prepare aluminosilicates with the MEI topology. Additionally, choline can be employed as the hydroxide or the chloride in concert with other inexpensive organoammonium hydroxides using the charge density mismatch concept to reduce costs even further. More than 30 years after the discovery of ZSM-18, little has been done with this zeolite. Finally, the approach disclosed here now makes the synthesis, study, and utility of MEI aluminosilicates accessible.

The UZM-22 aluminosilicate zeolite, which is obtained from the above-described process, is characterized by the x-ray diffraction pattern, having at least the d-spacings and relative intensities set forth in Table A below.

TABLE A

| 2θ | d (Å) | I/Io % |
|---|---|---|
| 7.53-7.89 | 11.73-11.20 | vs |
| 9.35-9.71 | 9.45-9.10 | w |
| 11.01-11.37 | 8.03-7.78 | m |
| 13.22-13.53 | 6.69-6.54 | w-m |
| 13.41-13.77 | 6.60-6.43 | w-m |
| 15.35-15.63 | 5.77-5.66 | w |
| 17.28-17.68 | 5.13-5.01 | w-m |
| 18.32-18.72 | 4.84-4.74 | w-m |
| 18.89-19.33 | 4.69-4.59 | m |
| 20.33-20.69 | 4.36-4.29 | w-m |

TABLE A-continued

| 2θ | d (Å) | I/Io % |
|---|---|---|
| 21.07-21.51 | 4.21-4.13 | s-vs |
| 21.34-21.74 | 4.16-4.08 | s-vs |
| 22.24-22.67 | 3.99-3.92 | w-m |
| 22.71-23.15 | 3.91-3.84 | w-m |
| 23.21-23.65 | 3.83-3.76 | m |
| 25.58-26.19 | 3.48-3.40 | w |
| 26.38-26.89 | 3.38-3.31 | m |
| 26.73-27.17 | 3.33-3.28 | w-m |
| 27.41-27.77 | 3.25-3.21 | w-m |
| 28.49-28.85 | 3.13-3.09 | m |
| 29.10-29.47 | 3.07-3.03 | m |
| 30.09-30.51 | 2.97-2.93 | w |
| 30.42-30.82 | 2.94-2.90 | w |
| 31.06-31.54 | 2.88-2.83 | w-m |
| 32.15-32.54 | 2.78-2.75 | w |
| 32.31-32.82 | 2.77-2.73 | w |
| 32.69-33.13 | 2.74-2.70 | w |
| 32.98-33.49 | 2.71-2.67 | w |
| 33.80-34.36 | 2.65-2.61 | w |
| 34.82-35.35 | 2.57-2.54 | w |
| 35.73-36.17 | 2.51-2.48 | w-m |
| 37.91-38.56 | 2.37-2.33 | w |

As will be shown in detail in the examples, the UZM-22 material is thermally stable up to a temperature of at least 400° C. and preferably up to about 600° C.

As synthesized, the UZM-22 material will contain some of the exchangeable or charge balancing cations in its pores. These exchangeable cations can be exchanged for other cations, or in the case of organic cations, they can be removed by heating under controlled conditions. Because UZM-22 is a large pore zeolite, it is also possible to remove some organic cations directly by ion exchange. The UZM-22 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4 in U.S. Pat. No. 6,776,975 B1 which is incorporated by reference in its entirety. Properties that are modified include porosity, adsorption, Si/Al ratio, acidity, thermal stability, etc.

The UZM-22 compositions which are modified by one or more techniques described in the '975 patent (herein UZM-22HS) are described by the empirical formula on an anhydrous basis of:

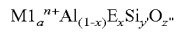

$M1_a^{n+}Al_{(1-x)}E_xSi_{y'}O_{z''}$ where M1 is at least one exchangeable cation selected from the group consisting of alkali, alkaline earth metals, rare earth metals, ammonium ion, hydrogen ion and mixtures thereof, "a" is the mole ratio of M1 to (Al+E) and varies from about 0.05 to about 50, "n" is the weighted average valence of M1 and has a value of about +1 to about +3, E is an element selected from the group consisting of gallium, iron, boron, and mixtures thereof, "x" is the mole fraction of E and varies from 0 to 1.0, y' is the mole ratio of Si to (Al+E) and varies from greater than about 4 to virtually pure silica and z' is the mole ratio of 0 to (Al+E) and has a value determined by the equation:

$z'=(a·n+3+4·y')/2$

By virtually pure silica is meant that virtually all the aluminum and/or the E metals have been removed from the framework. It is well know that it is virtually impossible to remove all the aluminum and/or E metal. Numerically, a zeolite is virtually pure silica when y' has a value of at least 3,000, preferably 10,000 and most preferably 20,000. Thus, ranges for y' are from 4 to 3,000 preferably greater than 10 to about 3,000; 4 to 10,000 preferably greater than 10 to about 10,000 and 4 to 20,000 preferably greater than 10 to about 20,000.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The UZM-22HS zeolite obtained after one or more of the above described treatments will have x-ray diffraction patterns which are different (and thus unique) from that of UZM-22. A list of the major peaks that are common to all the UZM-22HS materials is given in Table B.

TABLE B

UZM-22HS

| 2θ | d(Å) | I/Io % |
|---|---|---|
| 7.69-7.93 | 11.49-11.14 | vs |
| 9.49-9.85 | 9.31-8.97 | w |
| 11.09-11.49 | 7.97-7.70 | m |
| 13.41-13.81 | 6.60-6.41 | w |
| 14.58-14.90 | 6.07-5.94 | w-m |
| 16.48-16.96 | 5.37-5.22 | w |
| 17.61-17.85 | 5.03-4.97 | w-m |
| 18.59-18.83 | 4.77-4.71 | w |
| 19.09-19.69 | 4.65-4.51 | w |
| 20.52-21.16 | 4.32-4.20 | w-m |
| 21.28-22.08 | 4.17-4.02 | m |
| 22.44-22.96 | 3.96-3.87 | w |
| 23.01-23.41 | 3.86-3.80 | w |
| 27.72-28.20 | 3.22-3.16 | w |
| 29.25-29.97 | 3.05-2.98 | w-m |
| 30.85-31.09 | 2.90-2.87 | w |
| 31.36-32.02 | 2.85-2.79 | w |

The crystalline UZM-22 zeolite of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species.

The UZM-22 zeolite of this invention can also be used as a catalyst or catalyst support in various hydrocarbon conversion processes. Hydrocarbon conversion processes are well known in the art and include cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanation and syngas shift process. Specific reaction conditions and the types of feeds which can be used in these processes are set forth in U.S. Pat. No. 4,310,440 and U.S. Pat. No. 4,440,871 which are incorporated by reference. Preferred hydrocarbon conversion processes are those in which hydrogen is a component such as hydrotreating or hydrofining, hydrogenation, hydrocracking, hydrodenitrogenation, hydrodesulfurization, etc.

Hydrocracking conditions typically include a temperature in the range of 400° to 1200° F. (204-649° C.), preferably between 600° and 950° F. (316-510° C.). Reaction pressures are in the range of atmospheric to about 3,500 psig (24,132 kPa g), preferably between 200 and 3000 psig (1379-20,685 kPa g). Contact times usually correspond to liquid hourly space velocities (LHSV) in the range of about 0.1 hr$^{-1}$ to 15 hr$^{-1}$, preferably between about 0.2 and 3 hr$^{-1}$. Hydrogen circulation rates are in the range of 1,000 to 50,000 standard cubic feet (scf) per barrel of charge (178-8,888 std. m$^3$/m$^3$), preferably between 2,000 and 30,000 scf per barrel of charge (355-5,333 std. m$^3$/m$^3$). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the UZM-22 composition using feedstocks such as gas oils, heavy naphthas, deasphalted crude oil residua, etc. with gasoline being the principal desired product. Temperature conditions of 850° to 1100° F., LHSV values of 0.5 to 10 and pressure conditions of from about 0 to 50 psig are suitable.

Alkylation of aromatics usually involves reacting an aromatic ($C_2$ to $C_{12}$), especially benzene, with a monoolefin to produce a linear alkyl substituted aromatic. The process is carried out at an aromatic:olefin (e.g., benzene:olefin) ratio of between 5:1 and 30:1, a LHSV of about 0.3 to about 6 hr$^{-1}$, a temperature of about 100° to about 250° C. and pressures of about 200 to about 1000 psig. Further details on apparatus may be found in U.S. Pat. No. 4,870,222 which is incorporated by reference.

Alkylation of isoparaffins with olefins to produce alkylates suitable as motor fuel components is carried out at temperatures of −30° to 40° C., pressures from about atmospheric to about 6,894 kPa (1,000 psig) and a weight hourly space velocity (WHSV) of 0.1 to about 120. Details on paraffin alkylation may be found in U.S. Pat. No. 5,157,196 and U.S. Pat. No. 5,157,197, which are incorporated by reference.

The following examples are presented in illustration of this invention and are not intended as undue limitations on the generally broad scope of the invention as set out in the appended claims.

The structure of the UZM-22 zeolite of this invention was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 70° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of 100×I/I$_o$, the above designations are defined as:

w=0-15; m=15-60:s=60-80 and vs=80-100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

Example 1

An aluminosilicate solution was prepared by first mixing 19.40 g aluminum hydroxide (27.78% Al) and 387.3 g choline hydroxide, 50% solution, with vigorous stirring. After thorough mixing, 300.0 g of Ludox™ AS-40 (40% SiO$_2$) was added. The reaction mixture was homogenized for an additional hour with a high speed mechanical stirrer and placed in an oven at 100° C. overnight. Analysis showed the resulting aluminosilicate solution contained 7.45 wt. % Si and 0.73 wt. % Al yielding a Si/Al ratio of 9.82.

The entire aluminosilicate solution (706.7 g) was continuously stirred and to it there was added dropwise an aqueous solution containing 13.02 g of formulation LiCl*9H$_2$O and 18.19 g of formulation Sr(NO$_3$)$_2$*20H$_2$O. The resulting reaction mixture was then homogenized for 1 hour, sealed in a Teflon™ bottle placed in an oven at 100° C. and reacted for 6 days.

The solid products were recovered by centrifugation, washed with de-ionized water and dried at 95° C. The product was identified as UZM-22 by xrd. Representative diffraction lines observed for the product are shown in Table 1. The product composition was determined by elemental analysis to consist of the following mole ratios: Si/Al=5.10, Li/Al=0.046, Sr/Al=0.149, C/N=5.37, N/Al=0.81.

Scanning Electron Microscopy (SEM) revealed crystals of log shaped morphology, approximately 100 by 350 nm in size. This sample was calcined at 560° C. for 12 hrs under nitrogen and then air. The BET surface area of the calcined UZM-22 was found to be 606 m$^2$/g with a micropore volume of 0.28 cc/g.

TABLE 1

| 2θ | d(Å) | I/I$_0$ % |
|---|---|---|
| 7.72 | 11.44 | vs |
| 9.51 | 9.30 | w |
| 11.20 | 7.90 | m |
| 13.36 | 6.62 | w |
| 13.60 | 6.51 | m |
| 15.45 | 5.73 | w |
| 17.50 | 5.06 | w |
| 18.51 | 4.79 | w |
| 19.12 | 4.64 | w |
| 20.52 | 4.32 | m |
| 21.30 | 4.17 | vs |
| 21.56 | 4.12 | s |
| 22.48 | 3.95 | m |
| 22.95 | 3.87 | m |
| 23.42 | 3.80 | m |
| 25.89 | 3.44 | w |

TABLE 1-continued

| 2θ | d(Å) | I/I$_0$ % |
|---|---|---|
| 26.64 | 3.34 | m |
| 26.99 | 3.30 | m |
| 27.58 | 3.23 | m |
| 28.66 | 3.11 | m |
| 29.28 | 3.05 | m |
| 30.34 | 2.94 | w |
| 30.62 | 2.92 | w |
| 31.32 | 2.85 | m |
| 31.94 | 2.80 | w |
| 32.31 | 2.77 | w |
| 32.58 | 2.75 | w |
| 32.89 | 2.72 | w |
| 33.26 | 2.69 | w |
| 34.12 | 2.63 | w |
| 35.12 | 2.55 | w |
| 35.98 | 2.49 | w |
| 38.28 | 2.35 | w |

Example 2

An aluminosilicate reaction solution was prepared by first mixing 19.40 g of aluminum hydroxide (27.78% Al) and 387.3 g of choline hydroxide (50% solution), while stirring vigorously. After thorough mixing, 300.0 g Ludox™ AS-40 (SiO$_2$, 40%) was added. The reaction mixture was homogenized for 1 hour with a high speed mechanical stirrer, sealed in a Teflon bottle and placed in an oven overnight at 100° C. Analysis showed the aluminosilicate solution contained 8.22 wt. % Si and 0.81 wt. % Al (Si/Al=9.76).

A 282.12 g portion of the above aluminosilicate solution was continuously stirred and to it there was added dropwise, a composite aqueous solution containing 5.20 g of LiCl*9H$_2$O and 7.27 g of Sr(NO$_3$)$_2$*20H$_2$O. After the addition was completed, the resulting reaction mixture was homogenized for 1 hour, transferred to a 500 cc Teflon bottle and reacted at 100° C. Portions of the reaction mixture were sampled at 5, 6, 7, and 10 days. The solid product from each of these samples was recovered by centrifugation, washed with de-ionized water and dried at 95° C. The products resulting from all four reactions were identified to be UZM-22 by xrd. Table 2 shows representative diffraction lines observed for the sample that was reacted for 5 days. Elemental analysis gave a product composition in mole ratios of: Si/Al=5.05, Li/Al=0.07, Sr/Al=0.178, C/N=5.07, N/Al=1.12.

TABLE 2

| 2θ | d(Å) | I/I$_0$ % |
|---|---|---|
| 7.72 | 11.45 | vs |
| 9.51 | 9.30 | w |
| 11.16 | 7.92 | m |
| 13.36 | 6.62 | w |
| 13.58 | 6.52 | m |
| 15.48 | 5.72 | w |
| 17.45 | 5.08 | w |
| 18.50 | 4.79 | w |
| 19.10 | 4.64 | m |
| 20.49 | 4.33 | m |
| 21.26 | 4.18 | vs |
| 21.54 | 4.12 | s |
| 22.45 | 3.96 | w |
| 22.90 | 3.88 | m |
| 23.42 | 3.80 | m |
| 25.90 | 3.44 | w |
| 26.62 | 3.35 | m |
| 26.96 | 3.30 | m |
| 27.53 | 3.24 | m |

TABLE 2-continued

| 2θ | d(Å) | I/I₀ % |
|---|---|---|
| 28.64 | 3.11 | m |
| 29.26 | 3.05 | m |
| 30.29 | 2.95 | w |
| 30.59 | 2.92 | w |
| 31.32 | 2.85 | m |
| 31.94 | 2.80 | w |
| 32.30 | 2.77 | w |
| 32.58 | 2.75 | w |
| 32.90 | 2.72 | w |
| 33.24 | 2.69 | w |
| 34.11 | 2.63 | w |
| 35.10 | 2.55 | w |
| 35.90 | 2.50 | w |
| 38.28 | 2.35 | w |

Example 3

An aluminosilicate solution was prepared by first mixing 76.83 g aluminum hydroxide (27.78% Al) and 880.37 g of choline hydroxide (47.1%) with vigorous stirring. To this mixture, 640.84 g colloidal silica, (Ludox AS-40, 40% $SiO_2$) was added, followed by the addition of 1.95 g distilled water. The reaction mixture was homogenized for 1 hr with a high-speed mechanical stirrer, and then aged in Teflon bottles overnight at 100° C. After the aging step, the resulting aluminosilicate solutions were recombined and analyzed, the analysis indicated a silicon content of 7.61 wt. % and 1.44 wt. % Al (Si/Al 5.08).

A 1600 g portion of the above aluminosilicate solution was treated in a dropwise fashion with a composite solution containing 26.33 g Sr $(NO_3)_2$ and 10.55 g of LiCl dissolved in 250.0 g distilled water while stirring vigorously. After a half-hour of homogenization the reaction mixture was transferred to a 2-L Teflon bottle which was placed in a 100° C. oven and the reaction mixture was digested for 6 days at autogenous pressures. The solid products were recovered by centrifugation, washed with de-ionized water, and dried at 100° C.

Characterization of the solid product by Powder X-ray Diffraction (XRD) showed the lines in the pattern to be those for the material designated UZM-22. Representative diffraction lines observed for the sample are given in Table 3. Scanning Electron Microscopy (SEM) showed the crystallites to consist of rods approximately 20-300 nm long. To obtain an acid form of the zeolite, the UZM-22 was ammonium ion-exchanged before calcination to remove alkali/alkaline earth metals. Ammonium ion-exchange was accomplished stirring the zeolite in an excess of 1.5 M $NH_4NO_3$ solution at 75° C. for 2 hrs. The ammonium exchanged product was found to have the following mole ratios as determined by elemental analysis: Si/Al=4.58, Sr/Al=0.16 and Li/Al=0.005. The BET surface area of the calcined material was 624 $m^2$/g and the micropore volume was 0.283 cc/g.

TABLE 3

| 2θ | d(Å) | I/I₀ % |
|---|---|---|
| 7.70 | 11.47 | vs |
| 9.50 | 9.30 | w |
| 11.16 | 7.92 | m |
| 13.38 | 6.61 | w |
| 13.56 | 6.52 | m |
| 15.44 | 5.73 | w |
| 17.48 | 5.07 | w |
| 18.52 | 4.79 | w |

TABLE 3-continued

| 2θ | d(Å) | I/I₀ % |
|---|---|---|
| 19.08 | 4.65 | m |
| 20.52 | 4.33 | m |
| 21.28 | 4.17 | vs |
| 21.52 | 4.13 | vs |
| 22.46 | 3.96 | m |
| 22.90 | 3.88 | m |
| 23.42 | 3.80 | m |
| 25.86 | 3.44 | w |
| 26.62 | 3.345 | m |
| 26.94 | 3.31 | m |
| 27.56 | 3.23 | w |
| 28.66 | 3.11 | m |
| 29.24 | 3.05 | m |
| 30.30 | 2.95 | w |
| 30.56 | 2.92 | w |
| 31.28 | 2.86 | m |
| 31.89 | 2.80 | w |
| 32.29 | 2.77 | w |
| 32.56 | 2.75 | w |
| 32.90 | 2.72 | w |
| 33.24 | 2.69 | w |
| 34.12 | 2.63 | w |
| 35.10 | 2.55 | w |
| 35.90 | 2.50 | w |
| 38.30 | 2.35 | w |

Example 4

An aluminosilicate solution was prepared by first mixing 154.54 g of aluminum hydroxide (27.78% Al) and 1646.20 g of choline hydroxide (47.1%) with vigorous stirring. To this mixture 1198.31 g of colloidal silica (Ludox AS-40, 40% $SiO_2$) was added, followed by the addition of 0.75 g distilled water. The reaction mixture was homogenized for 1 hr with a high-speed mechanical stirrer, and then aged in Teflon bottles overnight at 100° C. After the aging step, the resulting aluminosilicate solutions were recombined and analyzed, the analysis indicated a silicon content of 7.62 wt. % and 1.43 wt. % Al (Si/Al=5.12).

A 1250 g portion of the above aluminosilicate solution was treated with a composite $Sr(NO_3)_2$/LiCl solution consisting of 21.01 g $Sr(NO_3)_2$ (99%) and 4.2 g of LiCl dissolved in 150.0 g distilled water in a dropwise fashion while applying vigorous mixing. The reaction mixture was homogenized for 30 minutes with a high speed mechanical stirrer. The reaction mixture was transferred to a 2-L Parr stainless steel stirred autoclave. The autoclave was heated to 103° C. and maintained at that temperature for 168 hr at autogenous pressure. The solid products were recovered by centrifugation, washed, and dried at 100° C.

Characterization of the solid product via powder x-ray diffraction showed the lines in the pattern to be those for the material designated UZM-22. Representative observed diffraction lines are given in Table 4 below. Elemental analysis showed the composition of the isolated product had the mole ratios of: Si/Al=4.89, Sr/Al=0.34, Li/Al=0.05. Scanning Electron Microscopy (SEM) showed the crystallites to consist of rods approximately 20-300 nm long. In order to obtain an acid form of the zeolite, the UZM-22 was ammonium ion-exchanged before calcination to remove alkali and alkaline earth metals. Ammonium ion-exchange was accomplished by stirring the zeolite in excess 1.5 M $NH_4NO_3$ solution at 75° C. for 2 hrs. The composition of the ammonium exchanged product exhibited the following mole ratios as determined by elemental analysis: Si/Al=5.75, Sr/Al=0.0006 and Li/Al=0.001.

TABLE 4

| 2θ | d(Å) | I/I₀% |
|---|---|---|
| 7.80 | 11.33 | vs |
| 9.62 | 9.19 | w |
| 11.28 | 7.84 | m |
| 13.46 | 6.58 | w |
| 13.68 | 6.47 | m |
| 15.56 | 5.69 | w |
| 17.58 | 5.04 | w |
| 18.62 | 4.76 | m |
| 19.22 | 4.61 | m |
| 20.60 | 4.31 | m |
| 21.40 | 4.15 | vs |
| 21.64 | 4.10 | vs |
| 22.56 | 3.94 | m |
| 23.04 | 3.86 | m |
| 23.54 | 3.78 | m |
| 26.04 | 3.42 | w |
| 26.76 | 3.33 | m |
| 27.06 | 3.29 | m |
| 27.68 | 3.22 | m |
| 28.76 | 3.10 | m |
| 29.38 | 3.04 | m |
| 30.40 | 2.94 | w |
| 30.72 | 2.91 | w |
| 31.42 | 2.84 | m |
| 32.06 | 2.79 | w |
| 32.44 | 2.76 | w |
| 32.69 | 2.74 | w |
| 33.02 | 2.71 | w |
| 33.36 | 2.68 | w |
| 34.22 | 2.62 | w |
| 35.22 | 2.55 | w |
| 36.06 | 2.49 | w |
| 38.40 | 2.34 | w |

Example 5

This example illustrates the use of seeds with an aluminosilicate solution. A 1200 g portion of the aluminosilicate solution prepared in Example 4 was treated with a composite $Sr(NO_3)_2$/LiCl solution containing 20.17 g $Sr(NO_3)_2$ (99%) and 4.04 g of LiCl dissolved in 120.0 g distilled water in a dropwise fashion with vigorous mixing. After the addition was complete, 10 g of UZM-22 seeds from a previous UZM-22 preparation were added. The resulting mixture was then homogenized for 30 minutes with a high speed mechanical stirrer. About 1400 g of the reaction mixture was transferred to a 2-L Parr stainless steel stirred autoclave where the mixture was reacted at 107° C. for 120 hrs. The solid product was recovered by centrifugation, washed with de-ionized water, and dried at 100° C.

Characterization of the solid product by powder x-ray diffraction (XRD) showed the lines in the pattern to be those for the material designated UZM-22. Representative diffraction lines observed for this sample are shown in Table 5 below. The composition of the isolated product had the following mole ratios Si/Al=4.77; Sr/Al=0.36, and Li/Al=0.06, as determined by elemental analysis. Scanning Electron Microscopy (SEM) showed the crystallites to consist of rods approximately 20-300 nm long. In order to obtain an acid form of UZM-22, it was ammonium ion-exchanged before calcination to remove alkali and alkaline earth metals. Ammonium ion-exchange was accomplished by stirring the zeolite in excess 1.5 M $NH_4NO_3$ solution at 75° C. for 2 hrs. The composition of the ammonium ion-exchanged product exhibited the following mole ratios as determined by elemental analysis: Si/Al=4.81; Sr/Al=0.014 and Li/Al=0.0009.

TABLE 5

| 2θ | d(Å) | I/I₀% |
|---|---|---|
| 7.78 | 11.36 | vs |
| 9.58 | 9.23 | w |
| 11.18 | 7.91 | m |
| 13.40 | 6.60 | w |
| 13.60 | 6.51 | m |
| 17.46 | 5.08 | w |
| 18.48 | 4.80 | w |
| 19.08 | 4.65 | m |
| 20.46 | 4.34 | m |
| 21.24 | 4.18 | vs |
| 21.46 | 4.14 | s |
| 22.42 | 3.96 | w |
| 22.82 | 3.89 | m |
| 23.34 | 3.81 | m |
| 25.87 | 3.44 | w |
| 26.58 | 3.35 | m |
| 26.95 | 3.30 | m |
| 27.52 | 3.24 | w |
| 28.58 | 3.12 | m |
| 29.22 | 3.05 | m |
| 30.54 | 2.92 | w |
| 31.28 | 2.86 | m |
| 32.24 | 2.77 | w |
| 32.80 | 2.73 | w |
| 33.18 | 2.70 | w |
| 35.84 | 2.50 | w |

Example 6

This example illustrates a gel approach using UZM-22 seeds. An aluminosilicate reaction mixture was prepared by adding 58.74 g of $Al(OH)_3$ (27.78% Al) to 624.93 g choline hydroxide (47.1%) with vigorous stirring. With continued stirring, 454.9 g colloidal silica (Ludox AS-40, 40% $SiO_2$) was added followed by the addition of a composite solution containing 19.28 g $Sr(NO_3)_2$ (97%) and 3.86 g LiCl dissolved in 188.29 g distilled water. The mixture was homogenized further for 30 minutes with a high-speed stirrer. Finally, 5 g of UZM-22 seeds were added with mixing continued for 30 minutes. A 1400 g portion of this reaction mixture was transferred to a 2-L Parr stainless steel stirred autoclave, which was heated to 107° C. and maintained at that temperature for 100 hrs. The solid product was recovered by centrifugation, washed with de-ionized water, and dried at 100° C.

Analysis by powder x-ray diffraction showed the product to have the UZM-22 structure. Representative lines in the observed diffraction pattern are given in Table 6. The composition of the isolated product had the following mole ratios: Si/Al=2.92, Sr/Al=0.61 and Li/Al=0.20. Scanning Electron Microscopy (SEM) showed the crystallites to consist of rods approximately 20-300 nm long. To obtain the acid form of UZM-22, it was ammonium ion-exchanged before calcination to remove alkali and alkaline earth metals. Ammonium exchange was accomplished by stirring the zeolite in excess 1.5 M $NH_4NO_3$ solution at 75° C. for 2 hrs. The composition of the ammonium ion-exchanged product was found to have the following mole ratios as determined by elemental analysis: Si/Al=3.15, Sr/Al=0.05 and Li/Al=0.069.

TABLE 6

| 2θ | d(Å) | I/I₀% |
|---|---|---|
| 7.62 | 11.59 | vs |
| 9.44 | 9.36 | w |
| 11.10 | 7.97 | m |

TABLE 6-continued

| 2θ | d(Å) | I/I₀ % |
|---|---|---|
| 13.30 | 6.65 | m |
| 13.50 | 6.55 | m |
| 15.42 | 5.74 | w |
| 17.38 | 5.10 | w |
| 18.42 | 4.81 | w |
| 19.00 | 4.67 | m |
| 20.42 | 4.35 | m |
| 21.18 | 4.19 | vs |
| 21.44 | 4.14 | s |
| 22.35 | 3.98 | m |
| 22.82 | 3.89 | m |
| 23.32 | 3.81 | m |
| 25.08 | 3.55 | m |
| 25.74 | 3.46 | w |
| 26.51 | 3.36 | m |
| 26.84 | 3.32 | m |
| 27.50 | 3.24 | w |
| 28.60 | 3.12 | m |
| 29.20 | 3.06 | m |
| 30.20 | 2.96 | w |
| 30.52 | 2.93 | w |
| 31.18 | 2.87 | m |
| 32.25 | 2.77 | w |
| 32.48 | 2.75 | w |
| 32.80 | 2.73 | w |
| 33.10 | 2.70 | w |
| 33.95 | 2.64 | w |
| 35.02 | 2.56 | w |
| 35.84 | 2.50 | w |
| 38.16 | 2.36 | w |

Example 7

To a 1200 g portion of the aluminosilicate solution prepared in Example 4, a composite aqueous $Sr(NO_3)_2$/LiCl solution containing 20.17 g $Sr(NO_3)_2$ (99%) and 4.04 g of LiCl dissolved in 120.0 g distilled water was added with vigorous stirring. Then 10 g of UZM-22 seeds were added and the reaction mixture was homogenized for an additional 30 minutes. A 1400 g portion of the reaction mixture was transferred to a 2-L Parr stainless steel stirred autoclave which was heated to 115° C. and maintained at that temperature for 99 hrs. The solid product was recovered by centrifugation, washed with de-ionized water, and dried at 100° C.

Characterization by powder X-ray diffraction (XRD) showed the lines in the pattern to be those for the material designated UZM-22. Representative diffraction lines observed for the product are given in Table 7. The composition of the isolated product had the mole ratios: Si/Al=4.69, Sr/Al=0.25 and Li/Al=0.69. Scanning Electron Microscopy (SEM) showed the crystallites to consist of rods approximately 20-300 nm long. To obtain the acid form of UZM-22, it was ammonium ion-exchanged before calcination to remove alkali and alkaline earth metals. Ammonium ion-exchange was accomplished by stirring the zeolite in excess 1.5 M $NH_4NO_3$ solution at 75° C. for 2 hrs. The composition of the ammonium ion-exchanged product had the following mole ratios as determined by elemental analysis: Si/Al=5.08, Sr/Al=0.0017 and Li/Al=0.001.

TABLE 7

| 2θ | d(Å) | I/I₀ % |
|---|---|---|
| 7.74 | 11.41 | vs |
| 9.57 | 9.23 | w |
| 11.20 | 7.89 | m |

TABLE 7-continued

| 2θ | d(Å) | I/I₀ % |
|---|---|---|
| 13.44 | 6.58 | w |
| 13.60 | 6.51 | m |
| 15.48 | 5.72 | w |
| 17.50 | 5.06 | w |
| 18.54 | 4.78 | w |
| 19.14 | 4.63 | m |
| 20.52 | 4.32 | m |
| 21.28 | 4.17 | vs |
| 21.54 | 4.12 | s |
| 22.48 | 3.95 | m |
| 22.92 | 3.88 | m |
| 23.40 | 3.80 | m |
| 25.88 | 3.44 | w |
| 26.64 | 3.34 | m |
| 26.98 | 3.30 | m |
| 27.56 | 3.23 | m |
| 28.66 | 3.11 | m |
| 29.30 | 3.05 | m |
| 30.28 | 2.95 | w |
| 30.58 | 2.92 | w |
| 31.34 | 2.85 | m |
| 32.32 | 2.77 | w |
| 32.54 | 2.75 | w |
| 32.92 | 2.72 | w |
| 33.25 | 2.69 | w |
| 34.08 | 2.63 | w |
| 35.12 | 2.55 | w |
| 35.96 | 2.50 | w |
| 38.26 | 2.35 | w |

Example 8

A 100.0 g portion of the aluminosilicate solution prepared in example 4 was treated in a dropwise fashion with a $Sr(NO_3)_2$ solution (1.64 g $Sr(NO_3)_2$ (99%)/15.0 g de-ionized water) while applying vigorous mixing. After a half-hour of homogenization the reaction mixture was transferred to a 100 ml Teflon-lined autoclave. The autoclave was placed in an oven set at 100° C. where the reaction mixture was reacted for 19 days at autogenous pressure. The solid product was recovered by centrifugation, washed with de-ionized water, and dried at 100° C.

Characterization by powder X-ray diffraction (XRD) showed the lines in the pattern to be those for the material designated UZM-22. Observed diffraction lines representative of the pattern are given in Table 8 below. The composition of the isolated product consisted of the mole ratios Si/Al=4.85, Sr/Al=0.44, Na/Al=0.01, N/Al=0.81. Scanning Electron Microscopy (SEM) showed the crystallites to consist of rods approximately 20-300 nm long.

TABLE 8

| 2θ | d(Å) | I/I₀ % |
|---|---|---|
| 7.76 | 11.38 | vs |
| 9.60 | 9.21 | w |
| 11.26 | 7.85 | m |
| 13.42 | 6.59 | w |
| 13.62 | 6.50 | m |
| 15.48 | 5.72 | w |
| 17.58 | 5.04 | w |
| 18.60 | 4.77 | w |
| 19.20 | 4.62 | m |
| 20.58 | 4.31 | m |
| 21.36 | 4.16 | vs |
| 21.60 | 4.11 | vs |
| 22.54 | 3.94 | m |
| 22.98 | 3.87 | m |

TABLE 8-continued

| 2θ | d(Å) | I/I₀ % |
|---|---|---|
| 23.46 | 3.79 | m |
| 25.35 | 3.51 | w |
| 25.98 | 3.43 | w |
| 26.70 | 3.34 | m |
| 26.98 | 3.30 | m |
| 27.64 | 3.23 | w |
| 28.70 | 3.11 | m |
| 29.32 | 3.04 | m |
| 30.34 | 2.94 | w |
| 30.68 | 2.91 | w |
| 31.42 | 2.85 | m |
| 31.92 | 2.80 | w |
| 32.38 | 2.76 | w |
| 32.62 | 2.74 | w |
| 32.98 | 2.71 | w |
| 33.36 | 2.68 | w |
| 34.12 | 2.63 | w |
| 35.14 | 2.55 | w |
| 35.98 | 2.49 | w |
| 38.34 | 2.35 | w |
| 40.06 | 2.25 | w |

Example 9

An aluminosilicate solution was prepared by first dissolving 77.94 g of aluminum hydroxide (27.78% Al) in 826.68 g choline hydroxide solution (50%) with vigorous stirring, followed by the addition of 600.0 g colloidal silica (Ludox AS-40, 40% $SiO_2$) and an additional hour of homogenization. The reaction mixture was sealed in Teflon bottles and reacted overnight at 100° C. The resulting aluminosilicate solutions were recombined and analyzed and were found to contain 7.88 wt % Si and 1.47 wt % Al (Si/Al=5.16).

A 300.0 g portion of the above mixture was stirred and to it there were added (dropwise) 16.71 g of a lithium chloride ($LiCl·9H_2O$) solution. Following the addition, the reaction mixture was homogenized for an additional hour, distributed among three Teflon bottles and reacted at 100° C. for 6 and 13 days, and 80° C. for 18 days. The solid products were recovered by centrifugation, washed with de-ionized water and dried at 95° C.

The products of this reaction initially formed UZM-4 (BPH), but converted over longer digestion times to UZM-22 (MEI). Via powder X-ray diffraction it was determined that the product resulting from the 6 day reaction showed a majority of UZM-4 with UZM-22 observable as a minor product. After 13 days at 100° C., the situation had reversed as UZM-22 was the major product contaminated with a slight UZM-4 impurity. Similarly, the 80° C. reaction yielded UZM-22 with a slight UZM-4 impurity after 18 days of digestion.

Example 10

This example describes the modification of a UZM-22 material. A 10 g portion of a UZM-22 sample (Si/Al=4.6) was calcined in a nitrogen atmosphere, ramping at 3° C./min to 560° C. and holding there for an additional hour before changing the atmosphere to air and continuing the calcination for another 8 hr. A solution was prepared by first diluting 2 g of $HNO_3$ (69%) followed by dissolving 10 g of $NH_4NO_3$ in 120 g de-ionized water. This solution was heated to 75° C. before adding the calcined UZM-22. The slurry was stirred for 1 hr at 75° C. The product was isolated by filtration, washed with de-ionized water and dried at 100° C. for 12 hrs.

The product was identified as UZM-22HS via x-ray powder diffraction. A representative set of the observed diffraction lines are given below in Table 9. Elemental analyses confirmed an increase in Si/Al ratio to Si/Al=6.9, while the $N_2$ adsorption measurements gave a BET surface area of 643 $m^2/g$ and a micropore volume of 0.31 cc/g.

TABLE 9

| 2θ | d(Å) | I/I₀ % |
|---|---|---|
| 7.84 | 11.26 | vs |
| 9.71 | 9.10 | w |
| 11.32 | 7.81 | m |
| 13.66 | 6.48 | w |
| 14.78 | 5.99 | m |
| 16.78 | 5.28 | w |
| 17.74 | 5.00 | w |
| 18.74 | 4.73 | w |
| 19.42 | 4.57 | w |
| 20.92 | 4.24 | w |
| 21.78 | 4.08 | m |
| 22.73 | 3.91 | w |
| 23.20 | 3.83 | w |
| 23.80 | 3.74 | m |
| 26.29 | 3.39 | w |
| 27.00 | 3.30 | m |
| 27.36 | 3.26 | w |
| 28.00 | 3.18 | w |
| 29.00 | 3.07 | w |
| 29.58 | 3.02 | w |
| 30.72 | 2.91 | w |
| 30.98 | 2.88 | w |
| 31.68 | 2.82 | w |

Example 11

This example demonstrates the modification of a UZM-22 material. A 40 g portion of a UZM-22 sample (Si/Al=4.6) was calcined under a nitrogen atmosphere by ramping at 3° C./min to 560° C. and holding there for 1 hr before changing the atmosphere to air and continuing the calcination for another 8 hr. Separately, a solution was prepared by diluting 8 g of $HNO_3$ (69%) followed by dissolving 40 g of $NH_4NO_3$ in 490 g de-ionized water. The solution was heated to 75° C. before adding the calcined UZM-22. The slurry was stirred for 1 hr at 75° C. The product was isolated by filtration, washed with de-ionized water and dried at 100° C. for 12 hrs.

The product was identified as UZM-22HS via x-ray powder diffraction. A representative set of the observed diffraction lines are given below in Table 10. Elemental analyses confirmed an increase in Si/Al ratio to Si/Al=7.2, while the $N_2$ adsorption measurements gave a BET surface area of 641 $m^2/g$ with a micropore volume of 0.30 cc/g.

TABLE 10

| 2θ | d(Å) | I/I₀ % |
|---|---|---|
| 7.78 | 11.35 | vs |
| 9.64 | 9.17 | w |
| 11.24 | 7.87 | m |
| 13.64 | 6.49 | w |
| 14.70 | 6.02 | m |
| 16.66 | 5.32 | w |
| 17.70 | 5.01 | w |
| 18.68 | 4.75 | w |
| 19.31 | 4.59 | w |
| 20.76 | 4.28 | m |
| 21.68 | 4.10 | m |
| 22.63 | 3.93 | w |
| 23.16 | 3.84 | w |
| 23.70 | 3.75 | m |
| 26.94 | 3.31 | m |
| 27.90 | 3.19 | w |

TABLE 10-continued

| 2θ | d(Å) | I/I₀ % |
|---|---|---|
| 29.52 | 3.02 | w |
| 30.94 | 2.89 | w |
| 31.58 | 2.83 | w |

Example 12

A 100 g portion of a UZM-22 sample (Si/Al=4.4) was steamed by ramping at 3° C./min to 550° C. in an air atmosphere containing 50% steam and held there for 6 hrs. Separately, a solution was prepared by diluting 30.69 g of HNO₃ (69%) followed by dissolving 66.5 g of NH₄NO₃ in 650.76 g de-ionized water. The solution was heated to 75° C. before adding 70 g of the steamed UZM-22. The slurry was stirred for 1 hr at 75° C. The product was isolated by filtration, washed with de-ionized water and dried at 100° C. for 12 hr.

The product was identified as UZM-22HS via x-ray powder diffraction. Representative observed lines in the diffraction pattern are shown in Table 11. Elemental analyses confirmed an increase in the Si/Al ratio to Si/Al=9.7, while the N₂ adsorption measurements gave a BET surface area of 522 m²/g with a micropore volume of 0.20 cc/g.

TABLE 11

| 2θ | d(Å) | I/I₀ % |
|---|---|---|
| 7.84 | 11.27 | vs |
| 9.62 | 9.18 | w |
| 11.34 | 7.80 | m |
| 13.58 | 6.51 | w |
| 14.72 | 6.01 | m |
| 16.70 | 5.30 | w |
| 17.72 | 5.00 | m |
| 18.73 | 4.73 | w |
| 19.46 | 4.56 | w |
| 20.80 | 4.27 | m |
| 21.66 | 4.10 | m |
| 21.86 | 4.06 | m |
| 22.76 | 3.9 | w |
| 23.26 | 3.82 | w |
| 23.78 | 3.74 | m |
| 27.06 | 3.29 | w |
| 27.38 | 3.26 | w |
| 28.02 | 3.18 | w |
| 29.12 | 3.06 | w |
| 29.70 | 3.01 | w |
| 30.80 | 2.90 | w |
| 31.00 | 2.88 | w |
| 31.78 | 2.81 | w |

Example 13

A sample of UZM-22 (125 g) (Si/Al=4.8) was steamed by ramping at 3° C./min to 550° C. in an air atmosphere containing 50% steam and held there for 6 hrs. A solution was prepared by diluting 46.04 g of HNO₃ (69%) followed by dissolving 99.75 g of NH₄NO₃ in 976.14 g de-ionized water. The solution was heated to 75° C. before adding 105 g of the steamed UZM-22. The slurry was stirred for 1 hr at 75° C. The product was isolated by filtration, washed with de-ionized water and dried at 100° C. for 12 hr.

The product was identified as UZM-22HS via x-ray powder diffraction. A representative set of the observed diffraction lines is given in Table 12 below. Elemental analyses confirmed an increase in the Si/Al ratio to Si/Al 12.12, while the N₂ adsorption measurements gave a BET surface area of 565 m²/g with a micropore volume of 0.21 cc/g.

TABLE 12

| 2θ | d(Å) | I/I₀ % |
|---|---|---|
| 7.82 | 11.30 | vs |
| 9.67 | 9.14 | w |
| 11.32 | 7.81 | m |
| 13.56 | 6.52 | w |
| 14.70 | 6.02 | m |
| 16.72 | 5.30 | w |
| 17.76 | 4.99 | m |
| 18.72 | 4.72 | w |
| 19.36 | 4.58 | w |
| 20.84 | 4.26 | m |
| 21.58 | 4.11 | m |
| 21.82 | 4.07 | m |
| 22.76 | 3.90 | w |
| 23.23 | 3.83 | w |
| 23.80 | 3.74 | m |
| 27.04 | 3.30 | w |
| 27.40 | 3.25 | w |
| 27.96 | 3.19 | w |
| 29.08 | 3.07 | w |
| 29.70 | 3.01 | w |
| 31.00 | 2.88 | w |
| 31.80 | 2.81 | w |
| 36.51 | 2.46 | w |

What is claimed is:

1. A microporous crystalline zeolite having a three-dimensional framework of at least AlO₂ and SiO₂ tetrahedral units and an empirical composition in the as synthesized and anhydrous basis expressed by an empirical formula of:

$$M_m^{n+}R_rAl_{1-x}E_xSi_yO_z$$

where M is at least one exchangeable cation selected from the group consisting of alkali, alkaline earth, and rare earth metals, "m" is the mole ratio of M to (Al+E) and varies from 0 to about 1.2, R is a singly charged organoammonium cation selected from the group of choline, ethyltrimethylammonium (ETMA), diethyldimethyl ammonium (DEDMA), tetraethyl ammonium (TEA), tetrapropylammonium (TPA), trimethylpropylammonium, trimethylbutylammonium, dimethyldiethanolammonium, and mixtures thereof, "r" is the mole ratio of R to (Al+E) and has a value of about 0.25 to about 2.0, "n" is the weighted average valence of M and has a value of about 1 to about 3, E is an element selected from the group consisting of gallium, iron, boron and mixtures thereof, "x" is the mole fraction of E and has a value from 0 to about 1.0, "y" is the mole ratio of Si to (Al+E) and varies from greater than 2 to about 12 and "z" is the mole ratio of O to (Al+E) and has a value determined by the equation:

$$z=(m \cdot n+r+3+4 \cdot y)/2$$

and is characterized in that it has the x-ray diffraction pattern having at least the d-spacings and intensities set forth in Table A:

TABLE A

| 2θ | d(Å) | I/I₀ % |
|---|---|---|
| 7.53-7.89 | 11.73-11.20 | vs |
| 9.35-9.71 | 9.45-9.10 | w |
| 11.01-11.37 | 8.03-7.78 | m |
| 13.22-13.53 | 6.69-6.54 | w-m |
| 13.41-13.77 | 6.60-6.43 | w-m |
| 15.35-15.63 | 5.77-5.66 | w |
| 17.28-17.68 | 5.13-5.01 | w-m |
| 18.32-18.72 | 4.84-4.74 | w-m |

TABLE A

| 2θ | d (Å) | I/I₀ % |
|---|---|---|
| 7.53-7.89 | 11.73-11.20 | vs |
| 9.35-9.71 | 9.45-9.10 | w |
| 11.01-11.37 | 8.03-7.78 | m |
| 13.22-13.53 | 6.69-6.54 | w-m |
| 13.41-13.77 | 6.60-6.43 | w-m |
| 15.35-15.63 | 5.77-5.66 | w |
| 17.28-17.68 | 5.13-5.01 | w-m |
| 18.32-18.72 | 4.84-4.74 | w-m |
| 18.89-19.33 | 4.69-4.59 | m |
| 20.33-20.69 | 4.36-4.29 | w-m |
| 21.07-21.51 | 4.21-4.13 | s-vs |
| 21.34-21.74 | 4.16-4.08 | s-vs |
| 22.24-22.67 | 3.99-3.92 | w-m |
| 22.71-23.15 | 3.91-3.84 | w-m |
| 23.21-23.65 | 3.83-3.76 | m |
| 25.58-26.19 | 3.48-3.40 | w |
| 26.38-26.89 | 3.38-3.31 | m |
| 26.73-27.17 | 3.33-3.28 | w-m |
| 27.41-27.77 | 3.25-3.21 | w-m |
| 28.49-28.85 | 3.13-3.09 | m |
| 29.10-29.47 | 3.07-3.03 | m |
| 30.09-30.51 | 2.97-2.93 | w |
| 30.42-30.82 | 2.94-2.90 | w |
| 31.06-31.54 | 2.88-2.83 | w-m |
| 32.15-32.54 | 2.78-2.75 | w |
| 32.31-32.82 | 2.77-2.73 | w |
| 32.69-33.13 | 2.74-2.70 | w |
| 32.98-33.49 | 2.71-2.67 | w |
| 33.80-34.36 | 2.65-2.61 | w |
| 34.82-35.35 | 2.57-2.54 | w |
| 35.73-36.17 | 2.51-2.48 | w-m |
| 37.91-38.56 | 2.37-2.33 | w | and is thermally stable up to a temperature of at least 400° C.

2. The zeolite of claim 1 where M is selected from the group consisting of lithium, sodium, potassium, rubidium, cesium, calcium, strontium, barium and mixtures thereof.

3. The zeolite of claim 1 where "x" is zero.

4. The zeolite of claim 1 where the zeolite is thermally stable up to a temperature of at least 600° C.

5. The zeolite of claim 1 where R is choline.

6. The zeolite of claim 1 where R is choline and M is selected from the group consisting of Li, Sr and mixtures thereof.

7. A process for preparing a microporous crystalline zeolite having a three-dimensional framework of at least $AlO_2$ and $SiO_2$ tetrahedral units and an empirical composition in the as synthesized and anhydrous basis expressed by an empirical formula of:

$$M_m^{n+}R_rAl_{1-x}E_xSi_yO_z$$

where M is at least one exchangeable cation selected from the group consisting of alkali, alkaline earth, and rare earth metals, "m" is the mole ratio of M to (Al+E) and varies from 0 to about 1.2, R is a singly charged organoammonium cation selected from the group choline, ethyltrimethylammonium (ETMA), diethyldimethyl ammonium (DEDMA), tetraethyl ammonium (TEA), tetrapropylammonium (TPA), trimethyl-propylammonium, trimethylbutylammonium, dimethyldiethanolammonium cations and mixtures thereof "r" is the mole ratio of R to (Al+E) and has a value of about 0.25 to about 2.0, "n" is the weighted average valence of M and has a value of about 1 to about 3, E is an element selected from the group consisting of gallium, iron, boron and mixtures thereof, "x" is the mole fraction of E and has a value from 0 to about 1.0, "y" is the mole ratio of Si to (Al+E) and varies from greater than 2 to about 12 and "z" is the mole ratio of O to (Al+E) and has a value determined by the equation:

$$z=(m \cdot n+r+3+4 \cdot y)/2$$

and is characterized in that it has the x-ray diffraction pattern having at least the d-spacings and intensities set forth in Table A:

and is thermally stable up to a temperature of at least 400° C.; the process comprising forming a reaction mixture containing reactive sources of M, R, Al, Si and optionally E and heating the reaction mixture at a temperature of about 60° C. to about 175° C., for a time sufficient to form the zeolite, the reaction mixture having a composition expressed in terms of mole ratios of the oxides of:

$$aM_{2/n}O:bR_{2/p}O:1-cAl_2O_3:cE_2O_3:dSiO_2:eH_2O$$

where "a" has a value of about 0.05 to about 1.25, "b" has a value of about 1.5 to about 40, "c" has a value of 0 to about 1.0, "d" has a value of about 4 to about 40, "e" has a value of about 25 to about 4000.

8. The process of claim 7 where M is selected from the group consisting of lithium, cesium, sodium, potassium, rubidium, strontium, barium and mixtures thereof.

9. The process of claim 7 where the source of M is selected from the group consisting of halide salts, nitrate salts, acetate salts, hydroxides, sulfate salts and mixtures thereof.

10. The process of claim 7 where the source of E is selected from the group consisting of alkali borates, boric acid, precipitated gallium oxyhydroxide, gallium sulfate, ferric sulfate, ferric chloride and mixtures thereof.

11. The process of claim 7 where the aluminum source is selected from the group consisting of aluminum isopropoxide, aluminum sec-butoxide, precipitated alumina, $Al(OH)_3$, aluminum metal and aluminum salts.

12. The process of claim 7 where the silicon source is selected from the group consisting of tetraethylorthosilicate, fumed silica, colloidal silica and precipitated silica.

13. The process of claim 7 where the reaction mixture is reacted at a temperature of about 80° C. to about 125° C. for a time of about 1 day to about 3 weeks.

14. The process of claim 7 where R is choline.

15. The process of claim 7 where R is choline and M is selected from the group consisting of Li, Sr and mixtures thereof.

16. The process of claim 7 where R is a combination of choline and at least one singly charged organoammonium cation selected from the group consisting of TEA, TPA, ETMA, DEDMA, trimethylpropylammonium, trimethylbutylammonium, or dimethyldiethanolammonium.

17. The process of claim 7 further comprising adding UZM-22 seeds to the reaction mixture.

* * * * *